US007968565B2

(12) United States Patent
Arkin et al.

(10) Patent No.: US 7,968,565 B2
(45) Date of Patent: Jun. 28, 2011

(54) THERAPEUTIC COMBINATIONS COMPRISING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID

(75) Inventors: Michelle Arkin, San Francisco, CA (US); Jennifer Hyde, San Francisco, CA (US); Duncan Walker, Moss Beach, CA (US); Jasmin Wright, San Francsico, CA (US)

(73) Assignee: Sunesis Pharmaceuticals, Inc., So. San Francisco, CA (US)

( * ) Notice: Subject to any disclaimer, the term of this patent is extended or adjusted under 35 U.S.C. 154(b) by 584 days.

(21) Appl. No.: 11/080,102

(22) Filed: Mar. 14, 2005

(65) Prior Publication Data

US 2005/0215583 A1    Sep. 29, 2005

Related U.S. Application Data

(60) Provisional application No. 60/553,578, filed on Mar. 15, 2004.

(51) Int. Cl.
*A61K 31/47* (2006.01)
*A61K 31/70* (2006.01)
(52) U.S. Cl. .......................... 514/300; 514/49
(58) Field of Classification Search .................. 514/47, 514/70
See application file for complete search history.

(56) References Cited

U.S. PATENT DOCUMENTS

| 4,261,989 | A | 4/1981 | Sasaki et al. .................. 514/183 |
|---|---|---|---|
| 5,817,669 | A | 10/1998 | Tomita et al. ................. 514/300 |
| 6,171,857 | B1 | 1/2001 | Hendrickson |
| 6,291,643 | B1 | 9/2001 | Zou et al. ....................... 530/350 |
| 6,570,002 | B1 | 5/2003 | Hardwick et al. ............ 536/23.1 |
| 6,641,810 | B2 | 11/2003 | Gold ............................ 424/145.1 |
| 6,670,144 | B1 | 12/2003 | Craig et al. ...................... 435/21 |
| 6,696,483 | B2 | 2/2004 | Singh ............................ 514/450 |
| 7,211,562 | B2 | 5/2007 | Rosen et al. |
| 2003/0165887 | A1 | 9/2003 | Reed |

FOREIGN PATENT DOCUMENTS

| JP | 09-221424 | 8/1997 |
|---|---|---|
| JP | 11-349565 | 12/1999 |
| WO | WO02/20500 A2 | 3/2002 |
| WO | WO2004/085418 A2 | 10/2004 |
| WO | WO2005/089756 A1 | 9/2005 |

OTHER PUBLICATIONS

Oxford Textbook of Oncology, 1995, vol. 1, pp. 445-453.*
Tomitra, Kyoji Synthesis and Structure-Activity Relationships of Novel 7-Substituted 1,4-Dihydro-4-oxo-1-(2-thiazolyl)-1,8-naphthyridine-3-carboxylic Acids as Antitumor Agents. Part 1, J. Med. Chem. 2002, vol. 45, pp. 5564-5575, 2002.
Tsuzuki, Yasunori et al., "Efficient stereospecific synthesis of (S,S)-3-methoxy-4-methylaminopyrrolidine", Tetrahedron: Asymmetry, vol. 12, pp. 1793-1799, 2001.
Tsuzuki, Yasunori et al., Synthesis and Structure-Activity Relationships of Novel 7-Substituted 1,4-Dihydro-4-oxo-1-(2-thiazolyl)-1,8-naphthyrldine-3-carboxylic Acids as Antitumor Agents. Part 2, vol. 47, pp. 2097-2109, 2004.
Jacob, Leonard S., "National Medical Series for Independent Study: Pharmacology", Fourth Edition, Chapter 11, pp. 253-274, 1996.
Patrick Therasse, et al., "New Guidelines to Evaluate the Response to Treatment in Solid Tumors", Journal of the National Cancer Institute, vol. 92, No. 3, Feb. 2, 2000.
Goodman & Gilman, The Pharmacological Basis of Therapeutics, McGraw-Hill Medical Publishing Division, Tenth Edition, pp. 1404-1411, 2001.
The Merck Manual (1999), p. 988.
Arbitrario, et al.. "SNS-595 A Novel S-Phase Active Cytotoxic Acts Synergistically With Cytarabine to Reduce Bone Marrow Cellularity and Circulating Neutrophils," *American Society of Hematology* conference, 2006.
Stockett et al., poster presentation at EORTC, 2009.
Chiba, et al., "Practical Synthesis of AG-7352, Optically Active New Antitumor Agent." Abstract, 218th ACS National Meeting, Aug. 22-26, 1999.
Evanchik, et al., "Non-Clinical Admet, PK, and Biological Activity of SNS-595, a Novel Cell Cycle Inhibitory Antineoplastic Agent." Drug metabolism reviews, Marcel Dekker,New York, NY, US, vol. 36, No. SUPPL1, Aug. 2004 (2004-2008), p. 103. XP008073741.
Kashimoto, et al., "Antitumor Activity of a Novel Quinolone Analog AG-7352 in Human Xenograft Models of Leukemia or Drug-Resistant Tumors and in an Experimental Metastatic Tumor Model." Proceedings of the Annual Meeting of the American Association for Cancer Research. New York, NY, vol. 42, Mar. 2001, p. 102-Abstract 553. XP008073722.
Lawrence, et al., "SNS-595, a Novel S-Phase Active Cytotoxic, Demonstrates Pharmacologic Properties Appropriate for the Treatment of Advanced Hematologic Malignancies." Blood, vol. 106, No. 11, Part 2, Nov. 2005, p. 2378. XP008073743.
Lawrence, et al., "SNS-595, A Novel S-Phase Active Cytotoxic, Exhibits Potent In Vitro and In Vivo Activies, and Has the Potential for Treating Advanced Hematoloic Malignancies." Proceedings of the Annual Meeting of the American Association for Cancer Research, New York, NY, Vo. 47, Apr. 2006, p. 1110.
Nakano, et al., "Antitumor Antitumor Activity of a Novel Quinolone DNA Topoisomerase II Inhibitor AG-7352." Proceedings of the Annual Meeting of the American Association for Cancer Research, New York, NY, vol. 40, Mar. 1999, p. 115-Abstract 767. XP008073720.
Sato, et al., "In Vivo Antitumor Activity of a Novel Quinolone Analogue AG-7352 Against a Borad-Spectrum of Cancers and Drug-Resistant Human Cancers." Abstract, 11th NCI-EOARTC-AACR symposium on new drugs in cancer therapy, Nov. 7-10, 2000.
Thirion, et al., "Interest of investigating p53 status in breast cancer by four different methods." Oncology Reports, vol. 9, No. 6, Nov. 2002, pp. 1167-1172.

(Continued)

*Primary Examiner* — James D Anderson
(74) *Attorney, Agent, or Firm* — Jones Day

(57) ABSTRACT

The present invention relates to SNS-595 and methods of treating cancer using the same.

1 Claim, 3 Drawing Sheets

OTHER PUBLICATIONS

Tomita, Kyoji Synthesis and Structure-Activity Relationships of Novel 7-Substituted 1-4-Dihydro-4-oxo-1-(2-thiaolyl)-1,8-naphthyrdine-3-carboxylic Acids as Antitumor Agents. Part 1, J. Med Chem. 2002, vol. 45 pp. 5564-5575, 2002.

Tomita, et al., "Synthesis and Antitumor Activity of Novel 7-Substituted 1,4-Dihydro-4-Oxo-1-(2-Thiazolyl)-1,8-Naphthyridine-3-Carboxylic Acids." Abstracts of Papers American Chemical Society, vol. 217, No. 1-2, 1999, p. MEDI 249.

Tsuzuki, et al., "Practical Synthesis of (3S,4S)-3-Methoxy-4-Methylaminopyrrolidine." Tetrahedron: Asymmetry 12(2001) 2989-2997.

Tsuzuki, et al., "Process Research of a Novel Quinolone Antitumor Agent, AG-7352." English Abstract, The Japanese Society for Process Chemistry, 2004 Summer Symposium.

Tsuzuki, et al., "Synthesis and Structure—Activity Relationships of 3-Substitued 1, 4-Dihydro-4-Oxo-1-(2-Thiazolyl)-1, 8-Naphthridines as Novel Antitumor Agents." Bioorganic & Medicinal Chemistry Letters 14 (2004): 3189-3193.

Tsuzuki, et al., "Synthesis of Optically Active Amine at C-7 Position of New Antitumor Agent AG-7352." Abstract, Molecular Chirality Conference, 1999.

Wright, et al., "SNS-595 Has Synergistic Activity in Vitro with DNA Damaging Agents and Antimetabolites." Proceedings of the Annual Meeting of the American Association for Cancer Research, New York, NY, vol. 47, Apr. 2006, p. 504. XP001199686.

JP09-221424 English Abstract, 1997.

JP11-349565 English Abstract, 1999.

* cited by examiner

THERAPEUTIC COMBINATIONS COMPRISING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID

This application claims priority to U.S. Ser. No. 60/553,578 filed Mar. 15, 2004 and is incorporated herein by reference.

SNS-595 is novel naphthyridine cytotoxic agent that was previously known as AG-7352 (see e.g., Tsuzuki et al., *Tetrahedron-Asymmetry* 12: 1793-1799 (2001) and U.S. Pat. No. 5,817,669). The chemical name of SNS-595 is (+)-1,4-dihydro-7-[(3S,4S)-3-methoxy-4-(methylamino)-1-pyrrolidinyl]-4-oxo-1-(2-thiazoyl)-1,8-naphthyridine-3-carboxylic acid and has the structure shown below

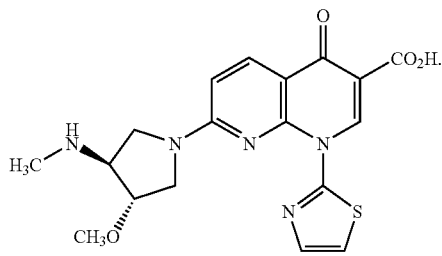

The present invention relates to SNS-595 and methods for maximizing its therapeutic potential to treat cancer.

DETAILED DESCRIPTION

Proliferating cells undergo four phases of the cell cycle: $G_1$, S, $G_2$, and M. These phases were first identified by observing dividing cells as the cells progressed through DNA synthesis which became known as the synthesis or S phase of the cell cycle and mitosis which became known as the mitotic or M phase or S phase of the cell cycle. The observed gaps in time between the completion of DNA synthesis and mitosis and between mitosis to the next cycle of DNA synthesis became known as the $G_1$ and $G_2$ phases respectfully. Non-proliferating cells that retain the ability to proliferate under the appropriate conditions are quiescent or in the $G_0$ state and are typically characterized as having exited the cell cycle.

The cell cycle has multiple checkpoints to prevent the cells from attempting to progress through the cell cycle under inappropriate circumstances by arresting the cells at these designated points. One important checkpoint occurs before the cell enters the S phase and tests, for example, whether the environment (e.g. sufficient nutrients) is suitable for cell division. Cells that fail a checkpoint in the $G_1$ phase and are thus prevented from entering the S phase are said to be in $G_1$ arrest. Another checkpoint occurs before the cell enters the M phase and test for example, the integrity of the synthesized DNA. Cells that fail a checkpoint in the $G_2$ phase and thus prevented from entering the M phase are said to be in $G_2$ arrest. Another checkpoint occurs during the M phase immediately before cytokinesis occurs and tests, for example, that the chromosomes are properly aligned. Cells that fail a checkpoint in the M phase and thus are prevented from dividing are said to be in M arrest.

In practice, cell cycle arrest is often characterized by DNA content and not by checkpoint failure. Consequently, the most often reported cell arrests are $G_1$ arrest based on 2N DNA content and the $G_2$/M arrest based on 4N DNA content.

SNS-595 is a cell cycle inhibitor and arrests cells at the $G_2$ interface. Initially, the activity of SNS-595 was believed due to topoisomerase II inhibition. Although SNS-595 is a catalytic inhibitor of topoisomerase II (inhibits decatenation and relaxation of supercoiled DNA with no formation of cleavable complexes) with an $IC_{50}$ of approximately 5 μM, a dose dependent correlation could not be established between its topoisomerase II activity and its effects in cells. For example, the $EC_{50}$ in various cells range from 200-300 nM, at least a ten-fold difference in increased potency from the biochemical inhibition of topoisomerase II. Moreover, when topoisomerase II levels in cells were modulated using 2-deoxyglucose (which results in the degradation of the enzyme), essentially no difference in activity was observed between the 2-deoxyglucose treated cells and untreated cells.

Figure 1:
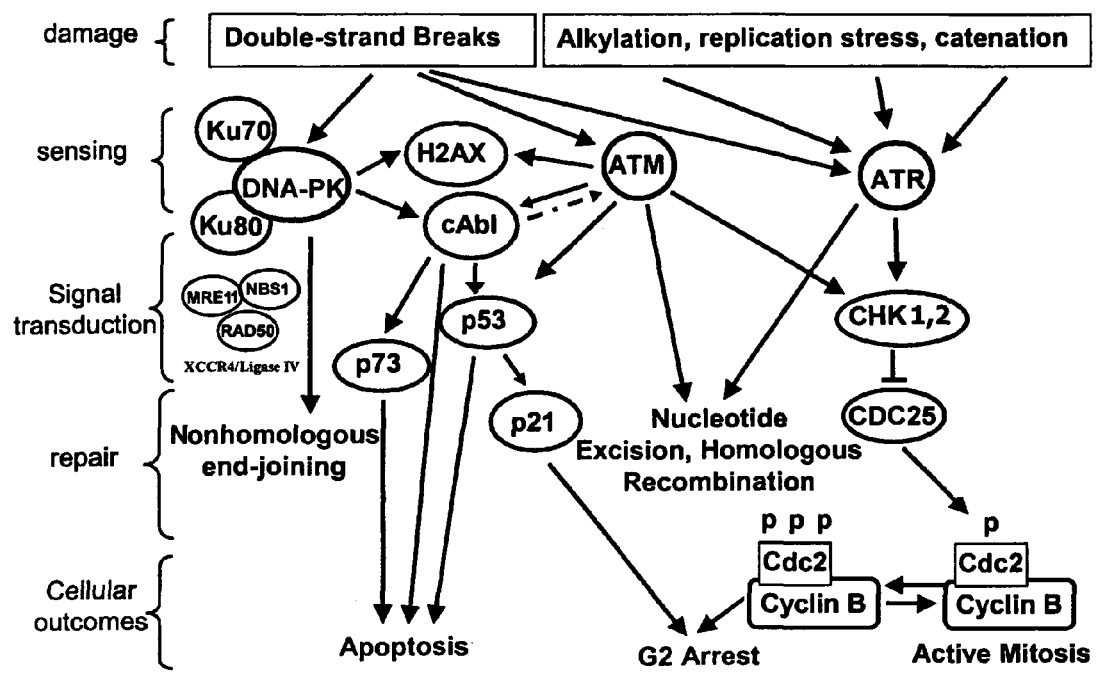
FIG. 1 illustrates the three major DNA damage and repair pathways.

The induction of $G_2$ arrest also does not appear to be the significant contributor to the cytotoxicity of SNS-595. For example, in cells where $G_2$ arrest is abrogated (by treating with caffeine which inhibits both ATM and ATR), essentially no difference in $EC_{50}$ values were observed upon treatment with SNS-595 when compared to the cells in the untreated group (not treated with caffeine and where $G_2$ arrest is observed). As shown by FIG. 1, ATM, ATR, and DNA-PK are three central DNA sensors/effectors that depending on the level of DNA damage that is detected within an individual cell, direct the cell into one of several outcomes including DNA repair, $G_2$ arrest or apoptosis.

Contrary to its initial characterization, SNS-595 mediates the activation of the DNA-PK pathway which eventually leads to apoptotic cell death. Notably, these events are S-phase specific meaning that they occur only during the S phase of the cell cycle.

Figure 2:
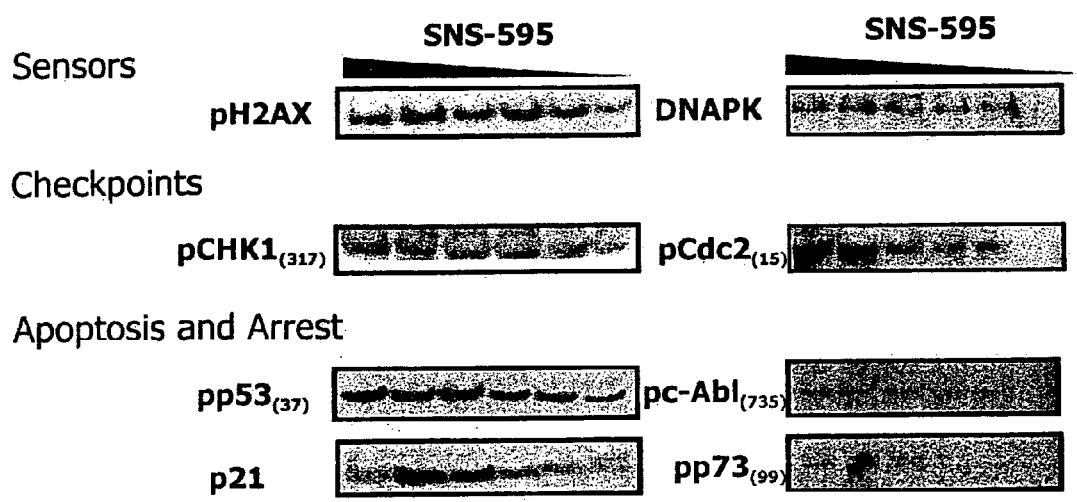
FIG. 2 depicts the dose-dependent responses of exemplary members of the DNA-PK pathway in HCT 116 cells treated with SNS-595.

Treatment with SNS-595 results in an increase in the number of double-strand DNA breaks that form during the S phase. This damage impedes the ability of the cell to synthesize DNA and lengthens the time the cell spends in the S phase. As FIG. 2 exemplifies, the formation of double-strand breaks activates, in a dose dependent manner, the DNA-PK mediated repair and apoptotic cellular machinery including but not limited to: i) DNA-PK expression; ii) H2AX phosphorylation; iii) c-Abl phosphorylation; iv) p53 phosphorylation; v) p73 phosphorylation; vi) p21 expression; vii) caspase-9 activation; and viii) caspase-3 activation. When the DNA damage is sufficiently severe such that the double-strand breaks cannot be repaired through non-homologous end joining (NHEJ), the cell rapidly enters apoptosis. Some cells are able to reach the $G_2$ phase but are subsequently arrested (mediated by cdc2/cyclin B) because the cells are too damaged to enter into the M phase and also eventually becomes apoptotic. Notably, because SNS-595 is S-phase selective, doses of SNS-595 that are cytotoxic to proliferating cells (thus are progressing through the cell cycle including the S phase) are non-lethal to non-proliferating cells.

Consistent with this mechanism, cells with induced resistance to SNS-595 also have alterations in the DNA-PK pathway. For example, a stable variant of HCT-116 cells that is approximately ten fold less sensitive to SNS-595 relative to HCT-116 cells, show for example increased levels of KU70, a protein that is an essential component of the activated DNA-PK complex. Conversely, decreased levels of DNA-PK or its activity (e.g. in the presence of an inhibitor) is associated with an increased sensitivity to SNS-595.

The DNA-PK mediated cytotoxicity of SNS-595 is unusual. Known compounds that also impede DNA synthesis usually act through ATR or through both ATM and DNA-PK. Illustrative examples of ATR mediated cytotoxic compounds include antimetabolites and DNA polymerase inhibitors. Illustrative examples of ATM and DNA-PK mediated cytotoxic compounds include topoisomerase II poisons and antineoplastic antibiotics such as bleomycin.

The present invention relates to SNS-595 and using its mechanism of action to maximize its therapeutic potential in treating human cancer.

Thus, in one aspect of the present invention, a method is provided for determining whether a cancer to be treated is likely to respond to SNS-595 treatment and if the treatment is pursued, whether the cancer is responding to SNS-595 treatment. The types of cancers that are suitable for treatment with SNS-595 include but are not limited to: bladder cancer, breast cancer, cervical cancer, colon cancer (including colorectal cancer), esophageal cancer, head and neck cancer, leukemia, liver cancer, lung cancer (both small cell and non-small cell), lymphoma, melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer.

The method comprises determining a first amount of at least one member of the DNA-PK pathway in cells of a cancer to be treated and comparing the first amount to a second amount.

When determining whether a cancer is likely to respond to SNS-595 treatment, the first amount is the amount of at least one member of the DNA-PK pathway in cells of a cancer to be treated (pretreatment amount). The second amount is the amount of a member of the DNA-PK pathway in reference cells (reference amount). Suitable reference cells include but are not limited to normal cells derived from the same tissue as the cancer to be treated. For example, if the cancer being treated is ovarian cancer, suitable reference cells include non-cancerous ovarian cells. The reference cells can be derived from the patient to be treated or can be derived from any normal tissue of the same type as the cancer being treated. Alternatively, the amount of any DNA-PK pathway member in HCT116 colon carcinoma cells (that have not been induced to show resistance to SNS-595) generally can be used as the reference amount.

Suitable members of the DNA-PK pathway for the practice of the invention include but are not limited to: DNA-PK; Ku70; Ku80; MRE11, NBS1, RAD50, XRCC4, ligase IV, H2AX, c-Abl, p53, p73, p21, caspase-9 and caspase-3. In one embodiment, the DNA-PK pathway member is DNA-PK. In another embodiment, the DNA-PK member is Ku70. In another embodiment, the DNA-PK pathway member is Ku80. In another embodiment, the DNA-PK pathway member is MRE11. In another embodiment, the DNA-PK pathway member is NBS1. In another embodiment, the DNA-PK pathway member is RAD50. In another embodiment, the DNA-PK pathway member is XRCC4. In another embodiment, the DNA-PK member is ligase IV. In another embodiment, the DNA-PK member is H2AX. In another embodiment, the DNA-PK member is c-Abl. In another embodiment, the DNA-PK member is p53. In another embodiment, the DNA-PK member is p73. In another embodiment, the DNA-PK member is p21. In yet another embodiment, the DNA-PK member is caspase-9. In yet another embodiment, the DNA-PK member is caspase-3.

The amount of a member of the DNA-PK pathway may be assessed directly such as quantifying the levels of the protein present in the cell. The amount of a particular member also may be assessed indirectly by measuring its corresponding DNA or mRNA levels. Alternatively, the amount of a particular member may also be indirectly measured using activity levels. An activity assay is an indirect measure because its enzymatic activity is being used as a surrogate for the amount of the enzyme. For example, when the member being assessed is a kinase, the amount of the kinase can be indirectly determined by determining the levels of its phosphorylation product (e.g., determine the amount of DNA-PK levels by determining the amount of H2AX phosphorylation levels). In addition to the above, the amounts of a member of the DNA-PK pathway can be assessed using any methods known in the art including immunohistochemistry.

If the pretreatment amount of the DNA-PK pathway member is less or approximately equal to the reference amount, then the cancer is likely to respond favorably to a dose of 10 $mg/m^2$-150 $mg/m^2$ of SNS-595. Body surface area (BSA) can be calculated using, for example, the Mosteller formula wherein:

$$BSA(m^2) = \text{square root of } [(\text{height(cm)} \times \text{weight(kg)}) / 3600].$$

In another embodiment, the dose of SNS-595 used to treat the cancer is 10 $mg/m^2$-100 $mg/m^2$. In another embodiment, the dose of SNS-595 used to treat the cancer is 30 $mg/m^2$-75 $mg/m^2$. In another embodiment, the dose of SNS-595 used to treat the cancer is 40 $mg/m^2$-80 $mg/m^2$. In another embodiment, the dose of SNS-595 used to treat the cancer is 50 $mg/m^2$-90 $mg/m^2$.

The administered dose of SNS-595 can be expressed in units other than as $mg/m^2$. For example, doses can be expressed as mg/kg. One of ordinary skill in the art would readily know how to convert doses from $mg/m^2$ to mg/kg to given either the height or weight of a subject or both (see e.g., http:///www.fda.gov/cder/cancer/animalframe.htm). For example, a dose of 10 $mg/m^2$-150 $mg/m^2$ for a 65 kg human is approximately equal to 0.26 mg/kg-3.95 mg/kg.

The administered dose can be delivered simultaneously or over a 24-hour period and may be repeated until the patient experiences stable disease or regression, or until the patient experiences disease progression or unacceptable toxicity. For example, stable disease for solid tumors generally means that the perpendicular diameter of measurable lesions has not increased by 25% or more from the last measurement. See e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of cancer cells that have been imaged using X-ray, CAT, PET, or MRI scan and other commonly accepted evaluation modalities.

If the pretreatment amount of the DNA-PK pathway member is more than the reference amount, SNS-595 as a single agent may not be sufficient and a combination therapy that includes SNS-595 should be considered.

When determining whether a cancer is responding to SNS-595 treatment, the first amount is the amount of at least one member of the DNA-PK pathway in cells of the cancer upon treatment with SNS-595 (post-treatment amount). The second amount is the amount of a member of the DNA-PK pathway in reference cells (reference amount). Preferably, the reference amount is the amount of the member of the DNA-PK pathway in cells of the cancer prior to treatment with SNS-595 (pretreatment amount). Other suitable reference cells include but are not limited to normal cells derived from the same tissue as the cancer to be treated. For example, if the cancer being treated is ovarian cancer, then suitable reference cells include non-cancerous ovarian cells. The reference cells can be derived from the patient to be treated or can be derived from any normal tissue of the same type as the cancer being treated. Alternatively, the amount of any DNA-PK pathway member in HCT116 colon carcinoma cells (that have not been induced to show resistance to SNS-595) generally can be used as the reference amount.

If the post-treatment amount is more than the reference amount then the cancer is responding favorably and treatment with SNS-595 (either as a single agent or as part of a combination) should continue.

In another aspect of the present invention, the mechanism of SNS-595 is used to provide combinations that maximize the therapeutic potential of SNS-595. In one embodiment, a combination is provided comprising:
 a) a therapeutically effective amount of SNS-595 and
 b) a therapeutically effective amount of a second agent that is capable of impeding DNA synthesis.

In contrast to the general rule that drugs with different mechanism of actions be selected to maximize the likelihood for additivity or synergy (see e.g., Page, R. and Takimoto, C., "Principles of Chemotherapy", Cancer Management: A Multidisciplinary Approach (2001), p. 23), combinations comprising SNS-595 and a second agent that also impedes DNA synthesis were found to be additive or synergistic.

As used herein, an agent impedes DNA synthesis when it directly or indirectly affects a cell's ability to synthesize DNA or to repair DNA damage. The agent can directly interact with DNA (e.g., bind to or intercalate with) or it can bind to a DNA-binding protein that is involved in DNA synthesis or DNA repair. In general, an agent that impedes DNA synthesis is active during the S phase but need not be S phase specific.

Suitable second agents include another agent that also mediates its cytotoxicity through the DNA-PK pathway. One example is an agent that inhibits nonhomologus endjoining repair such as DNA-PK inhibitors. As used herein, a DNA-PK pathway inhibitor is an agent that inhibits a signaling pathway mediated by DNA-PK. The inhibition of the activity of DNA-PK may be direct such as a catalytic inhibitor of DNA-PK itself or it may be indirect such as an agent that interferes with the formation of the active DNA-PK complex comprising DNA-PK, Ku70 and Ku80. Other examples of agents that mediate its cytotoxicity through the DNA-PK pathway include ligase IV inhibitors as well as apoptosis enhancing agents such as caspase-9 activators, caspase-3 activators and Hsp90 inhibitors.

Other examples of agents that impede DNA synthesis include other anti-cancer agents such as: alkylating agents, anti-neoplastic antibiotics, anti-metabolites, platinum coordination complexes, topoisomerase II inhibitors, and radiation. Standard doses and dosing regiments for these types of compounds are known (see e.g., The Physician's Desk Reference, Medical Economics Company, Inc. Montvale, N.J., 59th Ed. (2005)). However, for the purposes of illustration, several examples are provided below.

Alkylating agents are non-phase specific anti-cancer agents and strong electrophiles. Typically, alkylating agents form covalent linkages by alkylating DNA moieties such as phosphate, amino, sulthydryl, hydroxyl, carboxyl, and imidazole groups. Examples of alkylating agents include but are not limited to: alkyl sulfonates such as busulfan; nitrogen mustards such as chlorambucil, cyclophosphamide and melphalan; nitrosoureas such as carmustine; and triazenes such as dacarbazine.

Anti-neoplastic antibiotics are generally non-phase specific anti-cancer agents that bind to or intercalate with DNA. Typically, such action results in stable DNA complexes or strand breakage. Examples of antibiotic anti-cancer agents include but are not limited to bleomycin, dactinomycin, daunorubicin and doxorubicin.

Anti-metabolite agents act at S or DNA synthesis phase of the cell cycle by inhibiting the synthesis of DNA or an intermediate thereof. Because S phase does not proceed, cell death follows. Illustrative examples of anti-metabolites include but are not limited to folate analogs, purine analogs, adenosine analogs, pyrimidine analogs, and substituted ureas. An example of a folate analog includes methotrexate and pemetrexed. Examples of purine analogs include mercatopurine and thioguanidine. Examples of adenosine analogs include cladribine and pentostatin. Examples of pyrimidine analogs include cytarabine, capecitabline, and fluorouracil.

Platinum coordination complexes are non-phase specific anti-cancer agents that interact with DNA. The platinum complexes enter tumor cells and form intra- and inter-strand cross links with DNA. The accumulation of DNA damage in such cells eventually results in cell death. Examples of platinum coordination complexes include but are not limited to carboplatin, cisplatin and oxaliplatin.

Topoisomerase II inhibitors typically affect cells in the $G_2$ phase of the cell cycle by forming a ternary complex with topoisomerase and DNA. For example, topoisomerase II poisons result in an accumulation of DNA strand breaks that eventually lead to cell death. Examples of topoisomerase II inhibitors include but are not limited to epipodophyllotoxins such as etoposide and teniposide.

In one embodiment, the second agent is an alkylating agent. In another embodiment, the alkylating agent is an alkyl sulfonate and the cancer being treated is leukemia or lymphoma. In another embodiment, the alkyl sulfonate is busulfan. In another embodiment, the alkyl sulfonate is busulfan and the therapeutically effective amount is a daily dose of at least 1 mg. In another embodiment, the alkyl sulfonate is busulfan and the therapeutically effective amount is a daily oral dose of between about 2 mg and 8 mg. In another embodiment, the alkyl sulfonate is busulfan and the therapeutically effective amount is a daily oral dose of between about 1 mg and about 3 mg.

In another embodiment, the alkylating agent is a nitrogen mustard and the cancer being treated is bladder cancer, breast cancer, Hodgkin's disease, leukemia, lung cancer, melanoma, ovarian cancer, or testicular cancer. In another embodiment, the nitrogen mustard is chlorambucil. In another embodiment, the nitrogen mustard is chlorambucil and the therapeutically effective amount is at least 0.1 mg/kg. In another embodiment, the nitrogen mustard is chlorambucil and the therapeutically effective amount is a daily oral dose of between about 0.1 mg/kg and about 0.2 mg/kg for three to six weeks. In another embodiment, the nitrogen mustard is chlorambucil and the therapeutically effective amount is a dose of 0.4 mg/kg every three to four weeks. In another embodiment, the nitrogen mustard is cyclophosphamide. In another embodiment, the nitrogen mustard is cyclophosphamide and the therapeutically effective amount is an intravenous dose of at least 10 mg/kg. In another embodiment, the nitrogen mustard is cyclophosphamide and the therapeutically effective amount is an intravenous dose between about 10 mg/kg and about 15 mg/kg every seven to ten days. In another embodiment, the nitrogen mustard is cyclophosphamide and the therapeutically effective amount is an oral daily dose between about 1 mg/kg and about 5 mg/kg. In another embodiment, the nitrogen mustard is melphalan. In another embodiment, the nitrogen mustard is melphalan and the therapeutically effective amount is a daily oral dose of at least 2 mg. In another embodiment, the nitrogen mustard is melphalan and the therapeutically effective amount is a daily oral dose of 6 mg for two to three weeks, no melphalan for two to four weeks and then a daily oral dose of between about 2 mg and about 4 mg. In another embodiment, the nitrogen mustard is melphalan and the therapeutically effective amount is a daily oral dose of 10 mg/m$^2$ for four days every four to six weeks.

In another embodiment, the alkylating agent is a nitrosourea and the cancer being treated is brain tumor, colorectal cancer, Hodgkin's disease, liver cancer, lung cancer, lymphoma, or melanoma. In another embodiment, the nitrosourea is carmustine. In another embodiment, the nitrosourea is carmustine and the therapeutically effective amount is at least 150 mg/m$^2$. In another embodiment, the nitrosourea is carmustine and the therapeutically effective amount is an intravenous dose between about 150 mg/m$^2$ and 200 mg/m$^2$ every six to eight weeks.

In another embodiment, the alkylating agent is a triazene and the cancer being treated is Hodgkin's disease, melanoma, neuroblastoma, or soft tissue sarcoma. In another embodiment, the triazene is dacarbazine. In another embodiment, the triazene is dacarbazine and the therapeutically effective amount is a daily intravenous dose of between about 2.0 mg/kg and about 4.5 mg/kg for ten days every four weeks. In another embodiment, the triazene is dacarbazine and the therapeutically effective amount is a daily intravenous dose of 250 mg/m$^2$ for five days every three weeks. In another embodiment, the triazene is dacarbazine and the therapeutically effective amount is an intravenous dose of 375 mg/m$^2$ every sixteen days. In another embodiment, the triazene is dacarbazine and the therapeutically effective amount is an intravenous dose of 150 mg/m$^2$ for five days every four weeks.

In another embodiment, the second agent is an anti-neoplastic antibiotic and the cancer being treated is bladder cancer, breast cancer, cervical cancer, head and neck cancer, Hodgkin's disease, leukemia, multiple myeloma, neuroblastoma, ovarian cancer, sarcoma, skin cancer, testicular cancer, or thyroid cancer. In another embodiment, the antibiotic is bleomycin. In another embodiment, the antibiotic is bleomycin and the therapeutically effective amount is at least 10 units/m$^2$. In another embodiment, the antibiotic is bleomycin and the therapeutically effective amount is an intravenous, subcutaneous, or intramuscular dose of between about 10 units/m$^2$ and about 20 units/m$^2$ weekly or twice weekly. In another embodiment, the antibiotic is dactinomycin. In another embodiment, the antibiotic is dactinomycin and the therapeutically effective amount is at least 0.01 mg/kg. In another embodiment, the antibiotic is dactinomycin and the therapeutically effective amount is a daily intravenous dose of between about 0.010 mg/kg and about 0.015 mg/kg for five days every three weeks. In another embodiment, the antibiotic is dactinomycin and the therapeutically effective amount is an intravenous dose of 2 mg/m$^2$ every three or four weeks. In another embodiment, the antibiotic is daunorubicin. In another embodiment, the antibiotic is daunorubicin and the therapeutically effective amount is at least 30 mg/m$^2$. In another embodiment, the antibiotic is daunorubicin and the therapeutically effective amount is a daily intravenous dose of between about 30 mg/m$^2$ and about 45 mg/m$^2$ for three days. In another embodiment, the antibiotic is a liposomal preparation of daunorubicin and the therapeutically effective amount is an intravenous dose of 40 mg/m$^2$ every two weeks. In another embodiment, the antibiotic is doxorubicin. In another embodiment, the antibiotic is doxorubicin and the therapeutically effective amount is at least 15 mg/m$^2$. In another embodiment, the antibiotic is doxorubicin and the therapeutically effective amount is an intravenous dose of between about 60 mg/m$^2$ and about 90 mg/m$^2$ every three weeks. In another embodiment, the antibiotic is doxorubicin and the therapeutically effective amount is a weekly intravenous dose of between about 15 mg/m$^2$ and about 20 mg/m$^2$. In another embodiment, the antibiotic is doxorubicin and the therapeutically effective amount is a cycle comprising a weekly intravenous dose of 30 mg/m$^2$ for two weeks followed by two weeks of no doxorubicin.

In another embodiment, the second agent is an anti-metabolite. In another embodiment, the anti-metabolite is a folate analog and the cancer being treated is breast cancer, head and neck cancer, leukemia, lung cancer, non-Hodgkin's lymphoma, or osteosarcoma. In another embodiment, the folate analog is methotrexate. In another embodiment, the folate analog is methotrexate and the therapeutically effective amount is at least 2.5 mg. In another embodiment, the folate analog is methotrexate and the therapeutically effective amount is a daily oral dose of between about 2.5 mg and about 5 mg. In another embodiment, the folate analog is methotrexate and the therapeutically effective amount is a twice-weekly dose of between about 5 mg/m$^2$ and about 25 mg/m$^2$. In another embodiment, the folate analog is methotrexate and the therapeutically effective amount is a weekly intravenous dose of 50 mg/m$^2$ every two to three weeks. In another embodiment, the folate analog is pemetrexed. In another embodiment, the folate analog is pemetrexed and the therapeutically effective amount is at least 300 mg/m$^2$. In another embodiment, the folate analog is pemetrexed and the therapeutically effective amount is an intravenous dose of between about 300 mg/m$^2$ and about 600 mg/m$^2$ every two or three weeks. In another embodiment, the folate analog is pemetrexed and the therapeutically effective amount is an intravenous dose of 500 mg/m$^2$ every three weeks.

In another embodiment, the anti-metabolite is a purine analog and the cancer being treated is colorectal cancer, leukemia, or myeloma. In another embodiment, the purine analog is mercaptopurine. In another embodiment, the purine analog is mercaptopurine and the therapeutically effective amount is at least 1.5 mg/kg. In another embodiment, the purine analog is mercaptopurine and the therapeutically effective amount is a daily oral dose of between about 1.5 mg/kg and about 5 mg/kg. In another embodiment, the purine analog is thioguanidine. In another embodiment, the purine analog is thioguanidine and the therapeutically effective amount is at least 2 mg/kg. In another embodiment, the purine analog is thioguanidine and the therapeutically effective amount is a daily oral dose of between about 2 mg/kg and about 3 mg/kg.

In another embodiment, the anti-metabolite is an adenosine analog and the cancer being treated is leukemia or lymphoma. In another embodiment, the adenosine analog is cladribine. In another embodiment, the adenosine analog is cladribine and the therapeutically effective amount is at least 0.09 mg/kg. In another embodiment, the adenosine analog is cladribine and the therapeutically effective amount is a daily intravenous dose of 0.09 mg/kg for seven days. In another embodiment, the adenosine analog is cladribine and the therapeutically effective amount is a daily intravenous dose of 4 mg/m$^2$ for seven days. In another embodiment, the adenosine analog is pentostatin. In another embodiment, the adenosine analog is pentostatin and the therapeutically effective amount is 4 mg/m². In another embodiment, the adenosine analog is pentostatin and the therapeutically effective amount is an intravenous dose of 4 mg/m² every other week. In another embodiment, the adenosine analog is pentostatin and the therapeutically effective amount is an intravenous dose of 4 mg/m² every three weeks.

In another embodiment, the anti-metabolite is a pyrimidine analog and the cancer being treated is bladder cancer, breast cancer, colorectal cancer, esophageal cancer, head and neck cancer, leukemia, liver cancer, lymphoma, ovarian cancer, pancreatic cancer, skin cancer, or stomach cancer. In another embodiment, the pyrimidine analog is cytarabine. In another embodiment, the pyrimidine analog is cytarabine and the therapeutically effective amount is at least 100 mg/m². In another embodiment the pyrimidine analog is cytarabine and the therapeutically effective amount is a daily intravenous dose of 100 mg/m² for seven days. In another embodiment, the pyrimidine analog is capecitabine. In another embodiment, the pyrimidine analog is capecitabine and the therapeutically effective amount is at least a daily dose of 2000 mg/m². In another embodiment, they pyrimidine analog is capecitabine and the therapeutically effective amount is a twice-daily oral dose of between about 1200 mg/m² and about 1300 mg/m² for 14 days. In another embodiment, the pyrimidine analog is capecitabine and the therapeutically effective amount is a three-week cycle wherein a twice-daily dose of about 1250 mg/m² is given for fourteen days followed by one week of rest. In another embodiment, the pyrimidine analog is fluorouracil. In another embodiment, the pyrimidine analog is fluorouracil and the therapeutically effective amount is at least 10 mg/kg. In another example, the pyrimidine analog is fluorouracil and the therapeutically effective amount is a daily intravenous dose of between about 300 mg/m² and about 500 mg/m² for at least three days. In another example, the pyrimidine analog is fluorouracil and the therapeutically effective amount is a daily intravenous dose of 12 mg/kg for three to five days. In another embodiment, the pyrimidine analog is fluorouracil and the therapeutically effective amount is a weekly intravenous dose of between about 10 mg/kg and about 15 mg/kg.

In another embodiment, the anti-metabolite is a substituted urea and the cancer being treated is head and neck cancer, leukemia, melanoma, or ovarian cancer. In another embodiment, the substituted urea is hydroxyurea. In another embodiment, the substituted urea is hydroxyurea and the therapeutically effective amount is at least 20 mg/kg. In another embodiment, the substituted urea is hydroxyurea and the therapeutically effective amount is an oral dose of 80 mg/kg every three days. In another embodiment, the substituted urea is hydroxyurea and the therapeutically effective amount is a daily oral dose of between about 20 mg/kg and about 30 mg/kg.

In another embodiment, the second agent is a platinum coordination complex and the cancer being treated is bladder cancer, breast cancer, cervical cancer, colon cancer, head and neck cancer, leukemia, lung cancer, lymphoma, ovarian cancer, sarcoma, testicular cancer, or uterine cancer. In another embodiment, the platinum coordination complex is carboplatin. In another embodiment, the platinum coordination complex is carboplatin and the therapeutically effective amount is at least 300 mg/m². In another embodiment, the platinum coordination complex is carboplatin and the therapeutically effective amount is at least 300 mg/m² every four weeks. In another embodiment, the platinum coordination complex is carboplatin and the therapeutically effective amount is 300 mg/m² every four weeks. In another embodiment, the platinum coordination complex is carboplatin and the therapeutically effective amount is at least 360 mg/m² every four weeks. In another embodiment, the platinum coordination complex is cisplatin. In another embodiment, the platinum coordination complex is cisplatin and the therapeutically effective amount is at least 20 mg/m². In another embodiment, the platinum coordination complex is cisplatin and the therapeutically effective amount is a daily intravenous dose of 20 mg/m² for four to five days every three to four weeks. In another embodiment, the platinum coordination complex is cisplatin and the therapeutically effective amount is an intravenous dose of 50 mg/m² every three weeks. In another embodiment, the platinum coordination complex is oxaliplatin. In another embodiment, the platinum coordination complex is oxaliplatin and the therapeutically effective amount is at least 75 mg/m². In another embodiment, the platinum coordination complex is oxaliplatin and the therapeutically effective amount is between about 50 mg/m² and about 100 mg/m². In another embodiment, the platinum coordination complex is oxaliplatin and the therapeutically effective amount is an IV infusion of between about 50 mg/m² and about 100 mg/m² every two weeks. In another embodiment, the platinum coordination complex is oxaliplatin and the therapeutically effective amount is an IV infusion of between about 80 mg/m² and about 90 mg/m² every two weeks. In another embodiment, the platinum coordination complex is oxaliplatin and the therapeutically effective amount is a two-hour IV infusion of 85 mg/m² every two weeks.

In another embodiment, the second agent is a topoisomerase II inhibitor and the cancer being treated is Hodgkin's disease, leukemia, small cell lung cancer, sarcoma, or testicular cancer. In another embodiment, the topoisomerase II inhibitor is etoposide. In another embodiment, the topoisomerase II inhibitor is etoposide and the therapeutically effective amount is at least 35 mg/m². In another embodiment, the topoisomerase II inhibitor is etoposide and the therapeutically effective amount is between about 50 mg/m² and about 100 mg/m². In another embodiment, the topoisomerase II inhibitor is etoposide and the therapeutically effective amount is an intravenous dose of between about 35 mg/m² and about 50 mg/m² a day at least three times in five days every three or four weeks. In another embodiment, the topoisomerase II inhibitor is etoposide and the therapeutically effective amount is an intravenous dose of between about 50 mg/m² and about 100 mg/m² a day at least three times in five days every three or four weeks. In another embodiment, the topoisomerase II inhibitor is etoposide and the therapeutically effective amount is an oral dose of 100 mg/m² a day at least three times in five days every three or four weeks. In another embodiment, the topoisomerase II inhibitor is teniposide. In another embodiment, the topoisomerase II inhibitor is teniposide and the therapeutically effective amount is at least 20 mg/m². In another embodiment, the topoisomerase II inhibitor is teniposide and the therapeutically effective amount is a weekly dose of 100 mg/m². In another embodiment, the topoisomerase II inhibitor is teniposide and the therapeutically effective amount is a twice weekly dose of 100 mg/m². In another embodiment, the topoisomerase II inhibitor is teniposide and the therapeutically effective amount is a daily dose of between about 20 mg/m² and about 60 mg/m² for five days. In another embodiment, the topoisomerase II inhibitor is teniposide and the therapeutically effective amount is a daily dose of between about 80 mg/m² and about 90 mg/mm² for five days.

All cited references are incorporated herein by reference.

Example 1

Pharmaceutical Composition Suitable for Injection or Intravenous Infusion

Acidic compositions (<pH 4) provided the appropriate balance of increased solubility of SNS-595 and desirable pharmaceutical properties (e.g. increased patient comfort by causing less irritation at the delivery site). An illustrative example of a suitable composition comprises: 10 mg SNS-595 per mL of aqueous solution of 4.5% sorbitol that is adjusted to pH 2.5 with methanesulfonic acid. One protocol for making such a solution includes the following for making a 100 mg/10 mL presentation: 100 mg of SNS-595 and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

Example 2

Pharmacokinetics of SNS-595 in Cancer Patients

SNS-595 was administered to enrolled patients for up to six cycles. A cycle is defined as a three-week period, with SNS-595 administered on the first day of each cycle (day 0), followed by at least 21 days of observation. SNS-595 was administered to cohorts of at least 3 patients and dose escalation occurred by sequential cohort. Doses of SNS-595 were linear with AUC∞ and its pharmacokinetic properties were remarkably consistent among patients in the same cohort. Table 1 shows the pharmacokinetic parameters derived from the patients' plasma concentrations of SNS-595 over time.

595 (20 or 40 mg/kg) in the tail vein or a saline vehicle. At prescribed time points (1, 2, 4, 8, 16, and 24 hours post dose), animals were anesthetized with $CO_2$, blood was taken via terminal cardiac puncture, and animals were sacrificed. Tumors were excised, pulverized using liquid nitrogen-cooled mortar and pestle, and flash-frozen in liquid nitrogen. Tumor lysates were made from pulverized samples by addition of lysis buffer.

The protein concentrations of the DNA-PK pathway members were determined by Western blots. Approximately 25 micrograms of protein was loaded per lane on an SDS-PAGE gel. Proteins were separated by gel electrophoresis, blotted onto nitrocellulose membranes, and detected using the following antibodies: H2AX, phosphorylated at S139 (Cell Signaling, catalog no. 2577L); p53, phosphorylated at S15 (Cell Signaling, catalog no. 9284S); p53, phosphorylated at S37 (Cell Signaling, catalog no. 9289S); p21 (Cell Signaling, catalog no. 2946); cdc2, phosphorylated at Y15 (Calbiochem, catalog no. 219437); cyclin B (Santa Cruz, catalog no.sc-594 (H-20)); p73, phosphorylated at Y99 (Cell Signaling, catalog no.4665L); cAbl, phosphorylated at T735 (Cell Signaling, catalog no. 2864S); and CHK1, phosphorylated at S317 (Cell Signaling, catalog no. 2344L).

Figure 3:
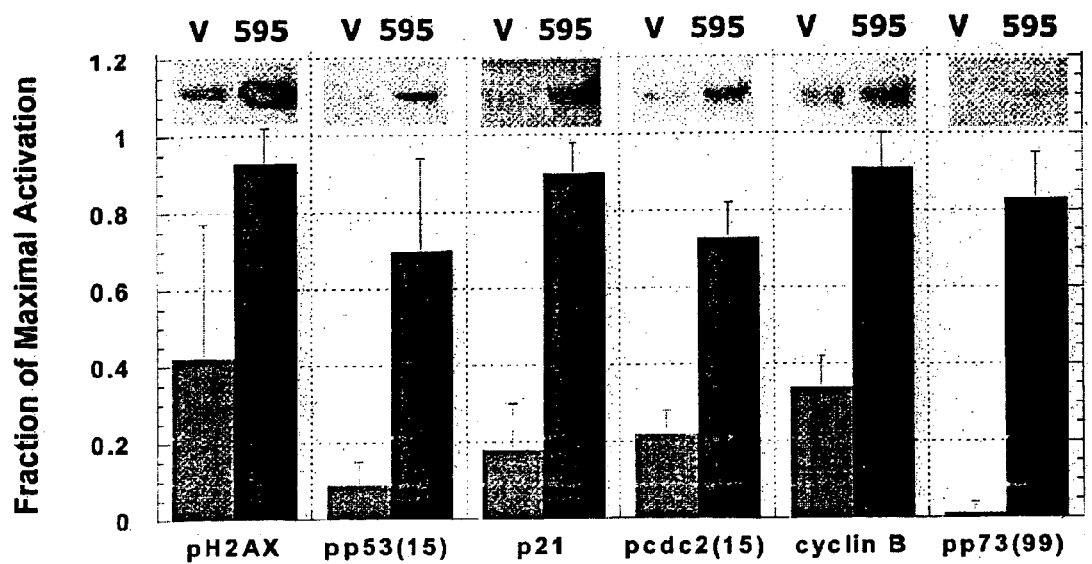
FIG. 3 depicts the activation of exemplary members of the DNA-PK pathway in tumors in mice.

FIG. 3 shows the levels of exemplary members of the DNA-PK pathway that were activated in tumors upon treatment with SNS-595.

Example 4

Combination Studies with SNS-595

HCT116 cells were plated at a density of approximately $4e^5$ cells/well with 100 µl/well of RPMI-1640 media (supplemented with 10% fetal bovine serum, 1% antibiotic/antimycotic and 1.5% sodium bicarbonate) in a 96-well clear tissue culture treated plate for 24 hours at 37° C., 5% $CO_2$. SNS-595 was then added to a final concentration between 5 µM and 5 nM either alone or mixed with another cytotoxic compound at a constant ratio. The final DMSO concentration was 1% in the assay plate. The treated cells were incubated for 72 hours at 37° C., 5% $CO_2$ before adding 20 µl/well 3-[4,5-dimethylthi-

TABLE 1

| Dose (mg/m2) | HL (hr) | C0 (ng/mL) | Cmax (ng/mL) | AUClast (hr*ng/mL) | AUCINF_obs (hr*ng/mL) | Cl_obs (mL/mln/kg) | Vz_obs (L/kg) | Vss_obs (L/kg) | MRTINF_obs (hr) |
|---|---|---|---|---|---|---|---|---|---|
| 3 | 16.27 | 152.25 | 138.80 | 750.08 | 1139.55 | 1.14 | 1.55 | 1.44 | 21.96 |
| SD | 4.871 | 82.282 | 80.566 | 87.622 | 263 | 0.318 | 0.297 | 0.277 | 6.836 |
| 6 | 20.69 | 376.69 | 347.00 | 2400.00 | 2990.29 | 0.71 | 1.28 | 1.24 | 29.05 |
| SD | 0.327 | 243.598 | 214.96 | 170.556 | 245.64 | 0.153 | 0.295 | 0.218 | 1.15 |
| 12 | 17.81 | 2888.66 | 2246.67 | 5395.53 | 6329.15 | 0.76 | 1.17 | 1.07 | 23.67 |
| SD | 3.898 | 1302.71 | 1065.145 | 292.281 | 181.804 | 0.126 | 0.258 | 0.184 | 5.021 |
| 24 | 16.14 | 2924.46 | 2703.33 | 11133.03 | 12655.32 | 0.83 | 1.15 | 1.06 | 21.65 |
| SD | 2.601 | 2884.702 | 2573.02 | 468.453 | 851.458 | 0.108 | 0.124 | 0.165 | 5.261 |
| 48 | 21.32 | 1984.52 | 2868.00 | 21098.53 | 27347.36 | 0.99 | 1.57 | 1.46 | 28.90 |
| SD | 6.32 | 189.677 | 2379.899 | 9405.346 | 14382.787 | 0.616 | 0.567 | 0.47 | 8.91 |
| 60 | 17.63 | 4797.47 | 4537.50 | 28112.17 | 33616.18 | 0.83 | 1.20 | 1.08 | 23.71 |
| SD | 4.15 | 2215.20 | 1947.89 | 9127.12 | 13081.44 | 0.352 | 0.37 | 0.218 | 6.93 |

Example 3

Pharmacodynamic Studies

Nu/nu mice (ca. 25 grams) were injected with HCT116 cells (which were obtained from the ATCC) in the hind flank at 5 million cells with 50% matrigel (Becton-Dickinson). Tumors were allowed to grow to 400 mm³. Xenograft bearing animals were then given either an IV bolus injection of SNSazol-2-yl]-2,5-diphenyltetrazolium bromide (MTT) for 1 hour followed by 100 µl/well N,N-dimethyl formamide/SDS lysis buffer for at least 16 hours. The plates were read for absorbance at a wavelength of 595 nm. The data was worked up using the median-effect method that quantifies the interaction using a Combination Index (calculated using the software for dose effect analysis, Calcusyn V2(Biosoft). A combination is said to be additive if it yields a Combination Index of 0.90-1.10. A combination is said to be synergistic if it yields a Combination Index less than 0.90 and a combination is said to be antagonistic if it yields a Combination Index of more than 1.10. All Combination Index calculations were at a Fa value of 0.5, the point where 50% of the cells were dead. See Table 2.

TABLE 2

| Compound | Mechanism | Combination Index @ Fa = 0.5 |
| --- | --- | --- |
| Etoposide | Topoisomerase II inhibitor | 0.44 |
| Daunomycin | Topoisomerase II inhibitor | 0.48 |
| 5-FU | Antimetabolite/pyrimidine analog | 0.39 |
| Cytarabine | Antimetabolite/pyrimidine antagonist | 0.61 |
| Methotrexate | Antimetabolite/anti-folate | 0.64 |
| Cisplatin | Platinum coordination complex | 0.54 |
| Carboplatin | Platinum coordination complex | 0.54 |
| Mitomycin C | Antibiotic/DNA alkylator | 0.63 |
| Actinomycin D | Antibiotic/DNA intercalator | 0.47 |
| Geldanamycin | Hsp90 inhibitor | 0.47 |
| Wortmannin | DNA-PK inhibitor | 0.42 |
| Olomucine | CDK inhibitor | 1.00 |
| Roscovitine | CDK inhibitor | 1.10 |
| Docetaxel | Microtubule stabilizing agent | 2.00 |

Example 5

HCT-116 colon cancer cells were plated at a density of approximately 4e5 cells/well with 100 µl/well of RPMI-1640 media (supplemented with 10% fetal bovine serum, 1% antibiotic/antimycotic, and 1.5% sodium bicarbonate) in a 96-well clear tissue-culture treated plate for 24 hours at 37° C., 5% $CO_2$. Some cells were treated with 100 nM wortmannin for 8-16 hours. SNS-595 was then added as a serial dilution, and cells were incubated for 72 hours at 37° C., 5% $CO_2$. MTT (20 µl/well of a 5 mg/ml stock solution) was added for 1 hour, followed by N,N-dimethyl formamide/SDS lysis buffer for at least 16 hours. Absorbance was monitored at 595 nm and data were fit by nonlinear regression to determine the inhibition of cell growth ($IC_{50}$) by SNS-595 in the absence and presence of wortmannin. The $IC_{50}$ for SNS-595 in HCT-116 cells was 3-6 fold lower in the presence of wortmannin than in its absence. Similar results were seen when DNA-PK null cell line (approximately a 10 fold sensitization) was used instead of HCT-116 cells.

What is claimed is:

1. A combination comprising: a) a therapeutically effective amount of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and b) a therapeutically effective amount of cytarabine.

* * * * *